United States Patent
Guo

(10) Patent No.: US 7,853,621 B2
(45) Date of Patent: Dec. 14, 2010

(54) INTEGRATING MEDICAL DATA AND IMAGES IN A DATABASE MANAGEMENT SYSTEM

(75) Inventor: Dongbai Guo, Nashua, NH (US)

(73) Assignee: Oracle International Corp., Redwood Shores, CA (US)

( * ) Notice: Subject to any disclaimer, the term of this patent is extended or adjusted under 35 U.S.C. 154(b) by 327 days.

(21) Appl. No.: 11/285,977

(22) Filed: Nov. 23, 2005

(65) Prior Publication Data

US 2007/0118540 A1 May 24, 2007

(51) Int. Cl.
*G06F 7/00* (2006.01)
*G06F 17/30* (2006.01)

(52) U.S. Cl. .................... 707/803; 707/999.1
(58) Field of Classification Search .......... 707/100
See application file for complete search history.

(56) References Cited

U.S. PATENT DOCUMENTS

| | | | |
|---|---|---|---|
| 6,725,231 B2 * | 4/2004 | Hu et al. | 707/102 |
| 7,099,876 B1 * | 8/2006 | Hetherington et al. | 707/100 |
| 7,149,750 B2 * | 12/2006 | Chadwick | 1/1 |
| 2002/0023172 A1 * | 2/2002 | Gendron et al. | 709/238 |
| 2002/0073236 A1 * | 6/2002 | Helgeson et al. | 709/246 |
| 2002/0083192 A1 * | 6/2002 | Alisuag | 709/237 |
| 2002/0143824 A1 * | 10/2002 | Lee et al. | 707/523 |
| 2004/0107210 A1 * | 6/2004 | Yang et al. | 707/104.1 |
| 2004/0205545 A1 * | 10/2004 | Bargeron et al. | 715/512 |
| 2004/0267788 A1 * | 12/2004 | Taniguchi et al. | 707/100 |
| 2005/0207658 A1 * | 9/2005 | Schofield | 382/232 |
| 2006/0013367 A1 * | 1/2006 | Sawyer et al. | 379/88.01 |
| 2006/0064328 A1 * | 3/2006 | Datta et al. | 705/3 |
| 2006/0282447 A1 * | 12/2006 | Hollebeek | 707/101 |
| 2008/0005059 A1 * | 1/2008 | Colang et al. | 707/1 |

OTHER PUBLICATIONS

Oracle interMedia User's Guide 10g Release 1(10.1), Dec. 2003.*

* cited by examiner

*Primary Examiner*—Mohammad Ali
*Assistant Examiner*—Griselle Corbo

(57) ABSTRACT

A method of integrating syntactically valid medical images into a database management system. A database table is created and a database object is initialized with a medical image object. The medical image object is parsed. An XML representation of metadata associated with the medical image object is created and the database object is inserted in the table.

21 Claims, 11 Drawing Sheets

| Study |
|---|
| General Study |
| Study Date |
| Patient Study |
| Clinical Trial Study |
| |
| DATETIME |
| PERSON_NAME |
| SEQUENCE |
| SHORT_STRING |
| SHORT_STRING |
| LONG_STRING |

— 251 (rows 2–5)
— 252 (rows 7–12)

FIG. 2B

INTEGRATING MEDICAL DATA AND IMAGES IN A DATABASE MANAGEMENT SYSTEM

BACKGROUND OF THE INVENTION

1. Field of the Invention

The present invention generally relates to the storage of medical data and in particular to providing medical imaging capabilities through a database management system.

2. Brief Description of Related Developments

Digital Imaging and Communications in Medicine ("DICOM") is the dominant standard for radiology imaging and communication. DICOM standardizes the data format and transfer protocol for data such as for example, images, waveforms, workflow messages and diagnostic reports. It is used in many fields of medicine, such as for example, radiology, cardiology and dentistry. The DICOM standard encompasses a large number of medical imaging modalities, such as for example computed tomography, magnetic resonance, ultrasound, positron emission tomography and digital radiography.

A DICOM object can store medical images, waveforms and diagnostic reports. A key concept of DICOM is to store metadata (attributes) along with image or waveform content. The metadata augments the image or waveform content with ownership, organization, imaging condition, layout, and workflow information. There is frequently a need to search DICOM images by this metadata or share the metadata with a popular web formatting specification such as extensible Markup Language ("XML"). In addition, there is also a need to share the image content with applications outside of a DICOM image repository (e.g. PACS).

DICOM was initiated by the American College of Radiology (ACR) to enhance the connectivity of radiological devices. Before DICOM became a widely adopted standard, each manufacturer had its own proprietary image format and communication protocol. It was almost impossible to produce third-party software to manage and/or study medical data. It was also impossible to connect devices from different manufacturers. In 1985, ACR and the National Electrical Manufacturers Association (NEMA) jointly published a medical imaging and communications standard, which was named the ACR-NEMA standard, to address this problem. Later in 1993, the standard went through major revisions and was renamed to DICOM (version 3.0). Since then, DICOM has dominated the field of radiology imaging and all major manufacturers conform to this standard. Today, any software component can take DICOM data from any manufacturer and manage the data with a uniform interface.

Like other standards, the DICOM standard is mostly developed by volunteers. Working groups formed by domain experts propose additions and changes to the existing standards and the changes are approved by a balloting process. Typically, NEMA publishes a new version of the standard each year on its web site [DICOMWEB] and the document is freely available for worldwide download.

The DICOM standard has two major areas of focuses: the data format and the communication/message protocol to exchange DICOM objects. The first part, the data format, is defined using object-oriented programming principles. Images and waveforms captured by an imaging device are represented as objects (information objects in DICOM terminology). Services (operations) such as "get" "find" and "store" may be defined on these objects. The services and the information objects are combined into service object pairs (SOPs). To send an object across the network or to encode the content of a DICOM object into a file, DICOM defines different types of transfer syntax (binary encoding rules). Transfer syntax specifies the mapping of a DICOM object hierarchy into a binary stream. The binary content can be stored on physical media such as tapes, CDs or floppy disks, and organized using the DICOM directory hierarchy. It can also be exchanged over a network with the DICOM communication protocol. The DICOM communication protocol covers the upper layers (application, presentation and session layer) of the OSI seven layer model (The DICOM communication protocol is typically implemented on top of TCP/IP). Recently, the DICOM standard introduces web access to DICOM objects (WADO), which covers HTTP access to a DICOM object storage. interMedia DICOM features primarily deal with the data format aspect of the DICOM standard.

Traditionally, medical information and data, such as for example DICOM objects, are stored in a (network) file system provided by an operating system. With the recent explosive growth in both the number and size of medical images, there has been an increasing need to manage DICOM objects with a database. When compared to the flat file system, a database offers better security, scalability and manageability. Database features such as backup, disaster recovery, and logical standby are also critical to medical applications. Objects managed in a database can be indexed to improve the efficiency of retrieval with Structured Query Language (SQL). Most modern databases are integrated with mid-tier applications such as a web server or an application server to facilitate the cross enterprise sharing of the data content.

However, a traditional database management system does not recognize medical data and information such as for example, DICOM objects natively. One cannot index DICOM objects or search them by their attributes. XML is widely used in metadata management applications. XML helps to reduce software development costs because of the wide range of tools available to create, edit, display, search and transform an XML document. XML is also easier to document and implement as well as integrate with other applications, such as for example HL7 V3 messaging and bioinformatics applications.

Previous attempts to map XML to DICOM have involved message exchange. The prior solutions provide a strong type of XML schema definition to rigorously constrain a DICOM information object. The result is a large number of complex XML schemas. It is very convenient to exchange an XML representation of a DICOM object and an XML document conforming to the XML schema definition will map to a conformant DICOM object. Due to the complexity of this type of XML mapping, it is inefficient to store/query/index their representation of metadata in a database management system.

It would therefore be advantageous to be able to define an XML representation of the metadata contained in medical data and images, such as DICOM objects, to facilitate the integration of medical data and images with database management systems ("DBMS").

To help reviewers better understand the rest of this document, some DICOM terminology is described below. Normative definitions can be found from [DICOM2004].

Standard attributes are the set of attributes defined by the DICOM standard committee, and are published in DICOM standard part 6. A standard attribute can be modified or deprecated by the standard committee at a later date. The number of standard attributes grows each year as the DICOM standard expands to new areas.

Private attributes are attributes defined by an organization and encoded in a DICOM object according to private attribute encoding rules. A private attribute can add modality-specific, manufacturer-specific or site-specific information to a DICOM object. Private attributes are not administered by the DICOM standard and are generally not known or used by any organization other than the one defining them.

Value representation is the DICOM standard's term for data type. The DICOM standard defines the following standard data types in part 5 of the standard: AE, AS, AT, CS, DA, DS, DT, FL, FD, IS, LO, LT, OB, OF, OW, PN, SH, SL, SQ, SS, ST, TM, UL, UN, US and UT.

Value multiplicity specifies how many times the value an attribute may repeat. It is part of the standard attribute specification (Part 6 of the DICOM standard).

An information object is an object-oriented representation of a real world entity in DICOM.

A service object pair (SOP) class models a category of information object and a set of operation associated with this information object.

A DICOM object is a binary stream or a standalone file that encodes a DICOM SOP class instance according to the DICOM standard. A DICOM object can store different types of data, such as patient administration information, a waveform, an image, a slice of a 3D volume, a video segment, a diagnostic report, a graphic or text annotation. A DICOM object contains a number of standard attributes. It may optionally contain private attributes.

Transfer syntax designates a particular way of encoding a DICOM object into a binary stream. It also specifies how the data content should be compressed. Examples of DICOM compression codec include JPEG, JPEG-LS, JPEG2000 and MPEG2.

A DICOM image refers any DICOM object that can be decomposed into 2D pixel arrays. Examples include a video segment, volume scan, and a single frame dental image. A DICOM image is always a DICOM object, but the converse is not true.

A unique identifier (UID) is a 64 byte dot-concatenated numeric string (like an IP address). It is a DICOM data type that is based on ISO object identifier (OID). It uniquely identifies a DICOM object worldwide. It is commonly constructed with a root that uniquely identifies an organization producing DICOM objects and a suffix that uniquely identifies a DICOM object within the organization.

Some other definitions include:

A SQL object is the database object that encapsulates a DICOM object. The SQL object has public member methods that permit the query and processing of a DICOM object.

Metadata extraction is the process of extracting attributes from a DICOM object.

A parser extracts metadata from a DICOM object into an in-memory structure.

Metadata encoding is the process of encoding the extracted DICOM attributes into an DICOM metadata document.

A (XML) metadata encoder converts the in-memory structure of the extracted DICOM attributes into an XML document.

Schema validation is the process of using an XML schema definition to validate an XML document that is constrained by the schema. With schema validation, one may confirm the correctness of the data type, data format, and hierarchy. Schema validation is generally only applicable to XML documents and not to DICOM objects.

Standard conformance is the syntactical and semantic consistency of a DICOM object with respect to the DICOM standard. The default constraint definition documents can generally define constraints that enforce the DICOM standard conformance.

Application conformance is the semantic consistency of a DICOM object with respect to application specific conformance rules, which may be stronger or weaker than the DICOM standard. An administrator may modify the default constraint document to enforce a different set of conformance rules to better suit the application.

Conformance validation is the process of checking the semantic conformance of a DICOM object to the DICOM standard against constraint definition documents.

A (DICOM) metadata document is an XML document that encodes the attributes extracted from a DICOM object. Each DICOM object maps to one metadata document. We provide methods to build a metadata document from a DICOM object. A DICOM metadata document has two sections. One section is the named section, where elements are organized by a predefined hierarchy and each element is addressable by a fixed XPath. We refer to attributes in this section as named attributes. The other section is the unnamed section, where the rest of the extracted attributes are organized and listed by their value representation. Each attribute in this section can be addressed with an XPath query of the element tag (in the form of /DATA_TYPE(tag='HHHHHHHH')). We refer to attributes in this section as unnamed attributes.

DICOM data type definition schema is an XML schema that defines the value representations (i.e. DICOM data types) given in the DICOM standard part 5. This data type definition schema is strongly coupled with DICOM parser. Any modification to this schema mandates data migration.

A metadata schema is the XML schema document that constrains the DICOM metadata document. This schema references the DICOM data type definition schema.

Standard data dictionary document is an XML document that lists the attributes defined by the DICOM standard. The DICOM standard data dictionary document is converted from the DICOM standard part 6. An administrator may update this document to reflect the most recent releases made by the DICOM standard committee.

Private data dictionary document lists private attributes. There are may be one or more private data dictionary documents. Each contains a set of private attribute definitions and its owning organization's UID. A private data dictionary document can be published by a third party. A database administrator may add new private data dictionary documents as they become available.

A (XML) mapping document is an XML document to define how each DICOM attribute should map to an element of the DICOM metadata document. The mapping document is used by the metadata encoder to produce a DICOM metadata document. Since the metadata document is constrained by the metadata schema, the mapping document must match the metadata schema and they can be derived from each other. We define a default mapping document that couples with the DICOM metadata schema. A database administrator may customize the mapping document and the metadata schema for each database instance.

Constraint definition documents are a set of XML documents that define groups of predicates to validate the conformance of a DICOM object or a DICOM metadata document. A constraint document should be based on the SOP class specification given in part 3 of the DICOM standard. It should specify attribute relationships and semantic constraint of an attribute that is not expressed by the DICOM metadata schema. An administrator may customize a constraint document to make it stronger, weaker or different from what have been defined by the DICOM standard.

Preference document specifies a set of the runtime preferences. We ship a default preference document. An administrator may update this document to change the run time behavior, such as changing the logging destination, turning on/off the logging of warning messages, and ignoring certain category of errors.

A configuration document is unique for each database instance and applicable to all DICOM objects stored in the database. Configuration documents are managed by the repository. Examples of configuration documents are data dictionary documents, the XML mapping document, constraint definition documents and a preference document.

A repository stores documents that are applicable to all SQL objects stored in a database instance. An administrator can access the repository and update the document stored in this repository. The changes made will affect the outcome of a method. Mapping document, data dictionary document and constraint document are examples of document stored in the repository. At runtime, a method will query the repository to get the latest copy of the document. For example, a database administrator updates an attribute definition in a data dictionary document and change its data type from DA (date) to DT (datatime). From there on, the parser will interpret this attribute as an instance of the DT (datatime) data type and the metadata encoder will encode this attribute as DT (datatime) in all future metadata documents.

DICOM volume scan is the set of images gathered in the single imaging operation. They can be stored as separate slices in multiple DICOM objects. Or they may be stored as a single DICOM multiframe object.

SUMMARY OF THE INVENTION

The disclosed embodiments are directed to a method of integrating syntactically valid medical images into a database management system. In one embodiment, a database table is created and a database object is initialized with a medical image object. The medical image object is parsed. An XML representation of metadata associated with the medical image object is created and the database object is inserted in the table.

In one aspect, the disclosed embodiments are directed to a of creating an XML schema definition for medical data media. In one embodiment the method includes defining shared attributes; defining application specific attributes; and mapping medical data media data types into XML schema data types.

In another aspect, the present invention is directed to a method for managing a DICOM object in a database. In one embodiment, the method includes defining a XML schema comprising a fixed core segment and an extensible segment, including attributes for all DICOM objects in the fixed core segment; and including a sequence of data element descriptors in the extensible segment.

BRIEF DESCRIPTION OF THE DRAWINGS

The foregoing aspects and other features of the present invention are explained in the following description, taken in connection with the accompanying drawings, wherein:

FIG. 2B is a block diagram of one embodiment of an attribute structure of an object incorporating features of the present invention.

DETAILED DESCRIPTION OF THE PREFERRED EMBODIMENT(s)

Figure 1:
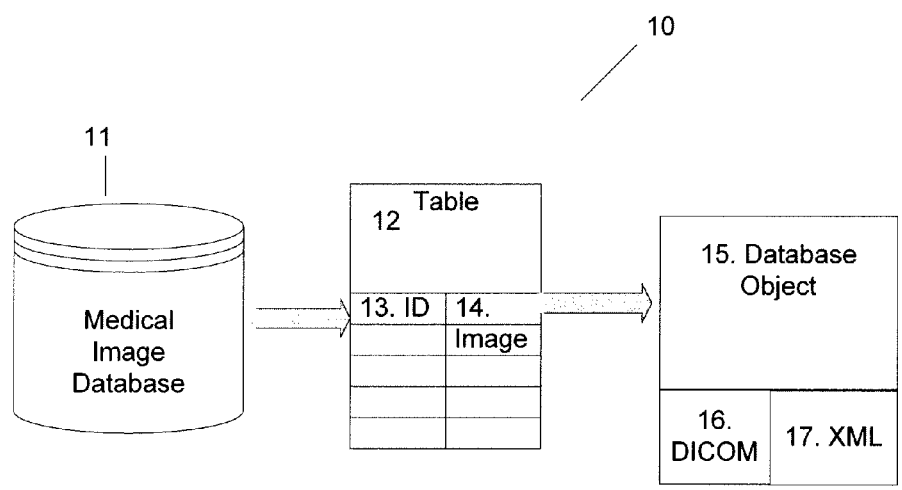
FIG. 1 is a block diagram of one embodiment of a system for mapping DICOM attributes to an XML schema definition incorporating features of the present invention.

Referring to FIG. 1, a block diagram of one embodiment a system 10 incorporating features of the disclosed embodiments is illustrated. Although the embodiments disclosed will be described with reference to the embodiments shown in the drawings, it should be understood that the embodiments disclosed can be embodied in many alternate forms of embodiments. in addition, any suitable size, shape or type of elements or materials could be used.

The disclosed embodiments generally define a unified XML representation of a medical information data object to integrate a medical data storage application to a database management system. For example, in one embodiment, when storing DICOM objects, it is cumbersome to define a separate XML schema for each object type because the DICOM standard does not define an XML mapping. Large numbers of schemas can complicate data management, and large documents with hundreds of attributes greatly impairs the usefulness and selectivity of the metadata. The unified XML schema definition of the disclosed embodiments can be used to represent any medical information or data object in a database. The features of the disclosed embodiments can also be used to represent DICOM objects in order to integrate a DICOM application to or with a database management system. Although the embodiments of the present invention will generally be described herein with reference to DICOM applications, the scope of the disclosed embodiments are not so limited and can be applied to any medical data, communication and information storage application or system.

The disclosed embodiments present an XML schema definition of the metadata for managing DICOM objects in a database. Although the disclosed embodiments are described in terms of XML, the scope of the present invention is not so limited, and XML is only one example of such a construct. The embodiments of the present invention can be used in conjunction with any image or data that is stored, in any particular format, that is mappable to XML.

The metadata is the set of attributes extracted or derived from an object that are needed to describe, organize and retrieve the object within or from the database. In one embodiment, the XML schema definition for representing any DICOM object in a database comprises a fixed core segment and an extensible segment. The fixed core segment can be composed of attributes that are either derivable or defined for all DICOM objects. These can include for example, patient, series and study. The extensible segment can be composed of a sequence of data element descriptors and supports unique requirements for specific DICOM implementations. These can include for example, version, modality and manufacturer or application specific attributes. By using this metadata definition, the DBMS functions can efficiently index, retrieve, manage and publish DICOM objects. XML is used as an intermediate representation of the DICOM metadata to facilitate the indexing and query of DICOM objects. Although reference is made herein to the use of XML and SQL objects that contain a member attribute that is an XML document, in alternate embodiments, the equivalent information can be stored in any suitable encoding format, such as for example, nested tables.

XML is used as an intermediate representation of the DICOM metadata to facilitate the indexing and query of DICOM objects within a database application. The disclosed embodiments map composite media storage service object pairs ("SOP"), which is the subset that are typically stored in an image archive and subsequently retrieved. The XML representation is transient and does not have to be persistently stored in a database management system. The XML representation must be stable and address database integration problems, such as for example, facilitating the indexing, querying and retrieval of medical image and data objects. XML permits the use of private attributes and allows easy customization and transformation.

Data types and encoding of the extracted metadata are converted into XML. The data type schema is tightly coupled with the underlying implementation. It is fixed and is released together with the application. The XML schema for the metadata document is user-configurable, which means the DICOM attributes, standard or private, can be mapped to any tree structure with user-configurable element names.

The separation of conformance validation and metadata encoding allows the use of a single XML schema to represent any DICOM objects. The XML document is simply a snapshot of what has been encoded into a DICOM object. All DICOM media storage object pair (SOP) objects share the same schema definition.

The single simplified schema representation reduces the number of distinct elements and the complexity of the XML schema, and thus increases the efficiency of the DICOM metadata management. The reason for this efficiency is that the complexity of the shredded storage of an XML schema based document increases with the complexity of the defining XML schema. DICOM objects from difference modalities can be managed in the same database table column. An application can quickly retrieve a DICOM object by its metadata. Although many DICOM objects are images, some are not, such as for example waveforms and radiology reports. The scope of the present invention applies to images, as well as waveforms and reports, for example.

Figure 2A:
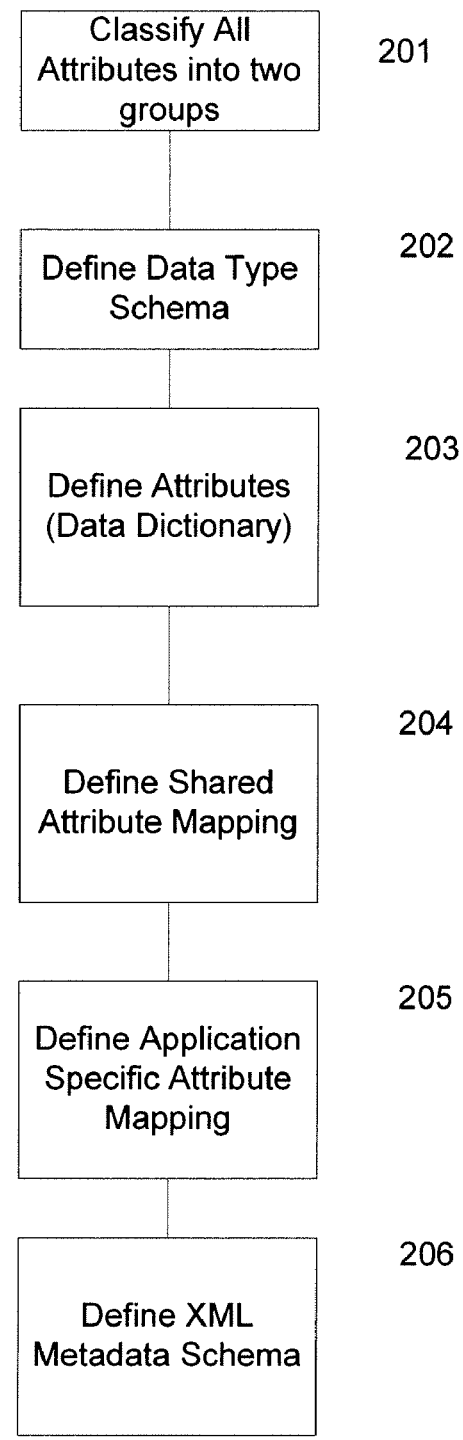
FIG. 2A is a flowchart of one embodiment of a method incorporating features of the present invention.

Referring to FIG. 2A, one embodiment of a method incorporating features of the present invention is illustrated. In this embodiment, one schema is used to represent all DICOM objects. Traditionally, multiple schemas are used to enforce strict standard conformance for information exchange. The disclosed embodiments allow one schema to be shared among all SOP classes to simplify query, data integration, documentation and implementation, and reduce computational cost. In order to manage DICOM object attributes, all DICOM attributes are classified 201 into two groups and the data type schema is identified 202. The first group is called named or shared attributes, which are selected standard attributes. Shared attributes generally comprise a fixed structure, fixed content and the DICOM SR structure is preserved. For example, the shared attributes can comprise a set of attributes that are addressable with XPath by a chain of human-readable element names and have a fixed path.

The second group is called unnamed or application specific attributes that are modality/SOP class specific and private attributes. Application specific attributes are generally flat list data items, extensible content, are strongly typed, attribute fully qualified and the sequence (SQ) structure is preserved. The application specific attributes are generally addressable by group and element tags (four-byte hexadecimal numbers). This classification is a relative concept, and in alternate embodiments an administrator can customize the classifications.

An attribute definer can be used to define 203 the attributes of the medical image. The shared attributes are mapped 204 and the application specific attributes are mapped 205. Once the XML mapping for both sets of attributes are defined, the XML metadata schema representing the medical image, or in one embodiment the DICOM objects, can be defined 206.

In one embodiment, shared attributes metadata information can include a file meta header, and SOP unique identifier and attributes that are common to all DICOM storage SOP classes. Examples can include, patient, study, series data, image, waveform, curve metadata, structured reports or small, standardized sets of data. Shared attribute data can generally often be present, is modality independent, stable and frequently queried.

Those DICOM attributes that are designated application specific attributes are generally modality specific, SOP class specific and private. The application specific attributes is a large and ever increasing set, very often absent, is application specific, volatile and not searched frequently. Examples can include attributes from X-Ray image modules, X-Ray acquisition modules or MR-diffusion modules. FIG. 2B illustrates an example of a shared attribute 251 and an application specific attribute 252.

For example, one instance of the database application 11 in FIG. 1 can define a named attribute "referring_physicians_name", which can be encoded under the "general_study" element of the named element group "/named/study" of a DICOM metadata document. The application 11 can use the path "/named/study/general_study/referring_physicians_name" to address this attribute. If, in a different application, this attribute is not critical to the application and is less frequently accessed, the application designer may define this attribute to be unnamed. It will then be listed among other attributes having the same data type, under an unnamed group "/unnamed" by its DICOM attribute tag "00080090". The application may still access this element by the path "/named/PERSON_NAME[attribute::tag='00080090']".

The purpose of this classification is to allow an application designer to customize the XML metadata schema to enhance the readability and the performance of his application. The metadata schema can be designed such that the named attributes are the smallest set that the application needs. Therefore the schema will be much simpler and more efficient to store and access than a generic schema defining all DICOM standard attributes. This design also allows a private attribute to be defined as a named attribute in the metadata schema and therefore simplifies the use of a private attribute. This permits efficient query of a private attribute in a database environment where many private attributes defined by different organizations coexist.

The data type schema are generally defined so that only DICOM-compatible data types are permitted in a DICOM metadata document. With this design definition, every attribute in a DICOM object can be mapped into an XML element, and every valid XML document can be mapped into a parsable DICOM object. This also allows an attribute to be converted between the named and unnamed type by direct cut-and-paste.

The disclosed embodiments generally provide for the lossless mapping between a DICOM object and a metadata document. A syntactically valid DICOM object can be mapped into a schema validated metadata document. The DICOM metadata document, combined with image or waveform data that can be optionally omitted, can be converted back into a syntactically valid DICOM object. The resultant DICOM object, after going through XML transformation, is semantically identical to the original. If the original DICOM object conforms to the DICOM standard, the result can be bitwise identical With standard-conformant data type: 1) Any valid metadata document can be translated into a syntactically valid DICOM object; an 2) Any syntactically valid DICOM object can be mapped into a valid XML document. The metadata schema can be customized by an application designer and is only dependent on the DICOM value representation definition. Unlike other parts of the DICOM standard, DICOM value representation is much more stable. As a result, the default or a customized XML metadata schema will remain valid even if the standard committee releases a new SOP class or modifies the existing ones. In other words, the XML metadata schema definition of the disclosed embodiments is a universal XML schema for all DICOM SOP class instances, because the XML metadata schema is not coupled with a particular DICOM standard release or a particular SOP class.

FIG. 1 illustrates one embodiment of a system 10 for managing a DICOM object with an object-relational database 11. The system 10 of FIG. 1 includes an object-relational database 11 and at least one relational table 12. The table 12 is a table that contains medical images and can be part of the database 11. As shown in FIG. 1, the table 12 includes two columns 13 and 14. Column 13 is a column for image ID (a primary key) and column 14 is a column for the DICOM image. The DICOM image column 14 stores a database object 15 representation of the DICOM object 16 and its XML metadata 17. The database object 15 contains functions to extract metadata from a DICOM object and to encode the metadata into a metadata document.

At initialization time, the database table 12 is created. A database object 15 is then initialized with a DICOM object. The database object 15 contains functions to parse a DICOM object and create an XML representation of the DICOM metadata. The database object 15 can be inserted into the table 12 and an index can be built on the image column 14. At runtime, a query can be issued on the database object 15. The query, such as searching for an image 16 by its DICOM unique identifier (SOP instance UID), can be translated into a query on its XML metadata 17. The same XML can be used to build a relational database. All DICOM objects share the same XML schema and all XML data can share the same database table column.

The metadata schema for the DICOM XML metadata is created and this schema is associated with the XML namespace designated to the default XML metadata schema. At runtime, when a DICOM object 16 is uploaded into the database 11, the DICOM object 16 will be stored within the database object 15, described herein as SQLDICOM. The XML metadata extraction function can be invoked at the same time the database object 15, SQLDICOM object is created or optionally at a later time. The database object 15 can be inserted into the table 12 with the proper ID 13 and an index can be built on its metadata content. At run time, a query can be issued on the table 12 to search for a particular DICOM object. The query on the SQLDICOM object 15 can be translated into a query on the XML metadata 17 of the DICOM object 16 stored in the SQLDICOM 15. The XML metadata query is easy to implement since most database management systems have integrated XML support.

The implementation framework and use case scenario described by FIG. 1 generally serves as an example. In alternate embodiments, one may build a pure relational database solution without using object-relational database technology.

In the framework of the disclosed embodiments, all DICOM objects share the same XML schema. Therefore, they can be stored in the same database table column.

Figure 3:
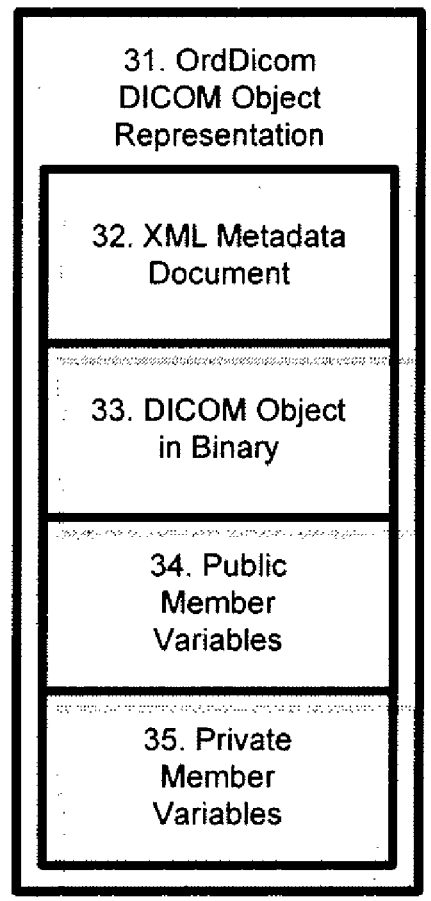
FIG. 3 is a block diagram of one embodiment of an object representation incorporating features of the present invention.

Referring to FIG. 3, one embodiment of the SQLDICOM object 15 of FIG. 1 is illustrated. The SQLDICOM object 31 is a database object definition that encapsulates a DICOM object. An SQLDICOM object 31 can embed a single DICOM storage SOP class object 33. The attributes in the DICOM object can be converted into a metadata document 32 and be stored persistently with the SQLDICOM object 31. The SQLDICOM object 31 may include public member variables 34, such as DICOM SOP class UID and DICOM SOP instance UID of the embedded DICOM object. The DICOM object 31 can also contain a set of private member variables 35. The term "private" is used to indicate that a variable's definition is opaque to a user of the SQLDICOM object 31, which store values derived from the embedded DICOM object 33. For example, if the embedded DICOM object 33 is an image, we may store a set of image descriptors such a pixel layout, color lookup table and frame-offset table to enable faster processing of image content, since the above information can be extracted with minimal cost at metadata extraction time. Note that, all public and private member variables of a database object are persistently stored. A user can directly dereference and access the DICOM object 33.

An SQLDICOM object 31 has many member functions, such as extracting metadata from the embedded DICOM object 33, compressing the embedded DICOM object 33, converting the embedded DICOM object 33 into a different type of transfer syntax, and converting the imbedded DICOM object 33 into an anonymized DICOM object. The member functions may benefit from data structures and information stored within the private member variables 35. With member functions, one may directly obtain a processed copy of the embedded DICOM object 33 from an SQLDICOM object 31. A sample application is to select a DICOM image from the database and to publish the DICOM image on the Web. The application may request a JPEG representation of the DICOM image at the publishing time, and the resulting JPEG image can be directly embedded into a web browser for easy sharing. The mid-tier application is simple and secure. The JPEG image can be generated on the fly or ahead of the time, and the transmission of data from the database server to the mid-tier is minimal.

Figure 4:
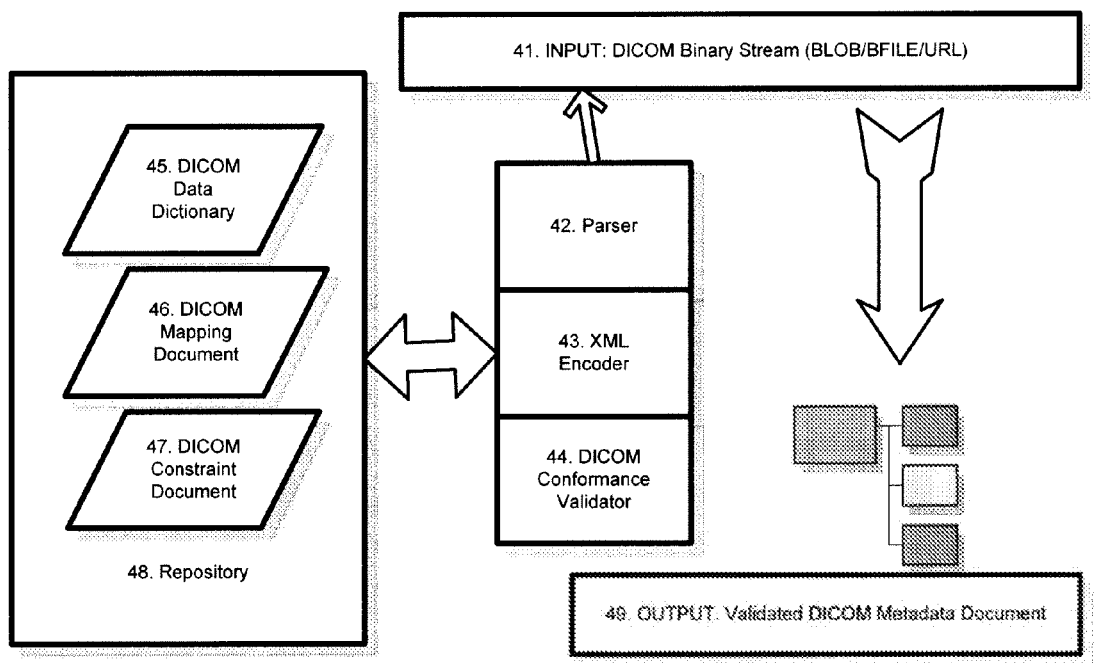
FIG. 4 is a block diagram of one embodiment of a process flow incorporating features of the present invention.

FIG. 4 illustrates one embodiment of the components involved in building a DICOM metadata document from a given DICOM object. The input 41 is a SQLDICOM object, such as object 15 of FIG. 1 that encapsulates a DICOM object 16. The DICOM object 16 can be stored for example, in a BLOB within the database, in a file on a local file storage system or in an external storage pointed to by an HTTP URL in the input 41. A repository 48 can store a number of configuration documents that are deployed at installation. These configuration documents can include for example, a data dictionary 45, a mapping document 46, and a constraint document 47. At run time, a parser 42 reads the content of a DICOM object 16. The parser requests from the repository 48 a set of DICOM attribute definitions that are contained in the data dictionary document 45. With the attribute definitions, the parser 42 converts the DICOM object 16 attribute into an array of attributes (an in-memory data structure). An XML metadata encoder 43 maps the in-memory representation of the DICOM attributes, for example, but not limited to, a hash table with attribute tags being the key, into a metadata document according to the mapping rules defined in the XML mapping document 46, which is also stored in the repository 48. The result metadata document is stored in the SQLDICOM object 15 shown in FIG. 1. The metadata document can be indexed and queried by keywords or XPATH query statements. In one embodiment, one may validate the standard conformance of an XML document with the DICOM conformance validator 44. The conformance is defined by one or more DICOM constraint documents 47, which can be customized for a particular application or a particular release of the DICOM standard. The final output is a schema-validated and standard or application conformant metadata document 49. The XML metadata can be persistently stored by the SQLDICOM object 15 described with reference to FIG. 1.

The metadata extraction function is a public method of the SQLDICOM. The method and the components involved can be implemented by a set of database stored procedures. The set of configuration documents managed by the repository 48 are part of the database installation, but can be customized by an administrator.

XML Schema Definition (XSD) for Data Types

The DICOM data types, which are called value representation (VR) in the DICOM standard, are mapped into XML schema based data types. Some DICOM VRs such as integer, float and datetime have corresponding built-in XSD data types and are straightforward to define. Some DICOM VRs such as person name and age string do not have obvious matching XML definitions and an XML schema data type needs to be defined for each of these VRs. In one embodiment, an XML schema data type incorporating features of the disclosed embodiments will facilitate the retrieval of a DICOM object based on its metadata content. For example, the VR type age string is defined in DICOM to be three digits followed by the letter "D" for day, "W" for week, "M" for month, and "Y" for year. Although a person can easily interpret this string, it is difficult to construct, implement, or perform a range search on an age string type. In the present invention, the XML schema definition for age string data type is defined to be a complex type containing the original string and an additional mandatory element "AGE_IN_DAYS", which is the age in number of days. The latter element maps to an integer type and can be used in a range search. Moreover, it can be easily indexed for efficient retrieval. The following code segment shows the definition of the VM type age string.

```
<?xml version="1.0" encoding="UTF-8"?>
<xs:schema xmlns="//xmlns.oracle.com/ord/dicom/datatype"
targetNamespace="//xmlns.oracle.com/ord/dicom/datatype"
xmlns:xs="//www.w3.org/2001/XMLSchema"
elementFormDefault="qualified"
attributeFormDefault="unqualified">
<!-- DICOM VM type Age String -->
<xs:complexType name="AS">
    <xs:sequence>
        <xs:element name="AGE_STRING"
            type="AgeString"/>
        <xs:element name="AGE_IN_DAYS"
```

-continued

```
            type="xs:unsignedInt"/>
    </xs:sequence>
</xs:complexType>
<xs:simpleType name="AgeString">
    <xs:restriction base="xs:token">
        <xs:pattern value='[0-9]{3}(D|W|M|Y)'/>
    </xs:restriction>
</xs:simpleType>
<!-- Other data type definitions are omitted -->
</xs:schema>
```

As is obvious from the above code segment, the XSD is defined to be strictly conformant to the DICOM VR definition. For example, an acceptable age data string is "007D", but not "007d" or "7D". Violations, such as strings longer than the defined length, will result in an XML document validation failure. Each DICOM VR type is also defined to explicitly list all subfields for convenient retrieval and improved readability. For example, when mapping the DICOM VR type person name, it is defined to be a complex type containing family name, given name, middle name, prefix and suffix. Each component is a complex type containing three subcomponents: unibyte, ideographic and phonetic. The complex type also contains an attribute that specifies person name type, which can take the value of "unibyte", "ideographic" or "phonetic".

It is necessary to special case the DICOM VR type sequence of items (SQ) and unknown (UN). The DICOM SQ type is equivalent to a universal container type. It can contain items that can be recursively SQ types. Since the containment relationship carries semantic significance, we retain the hierarchy when encoding an "SQ" attribute in XML whether an SQ type appears as a named or an unnamed attribute.

DICOM Data Dictionary

The DICOM standard defines the standard set of attributes that can be embedded in a DICOM object. To convert the metadata content of a DICOM object into XML, the group and element number (Tag), standard name (Name), value representation (VR), how many time it may repeat (VM) and whether or not it has been retired (deprecated), needs to be known about each attribute. A standard data dictionary document can be used to store this information and expose its definition to the user of the database so that they can modify this document whenever there is a change announced by the DICOM standards committee. Examples of attribute definitions are:

| Tag | Name | VR | VM | Retired |
|---|---|---|---|---|
| (0008, 0115) | Coding Scheme Name | ST | 1 | — |
| (0008, 1000) | Network ID | — | — | RET |

The above definition will be translated into the following XML elements:

```
<STANDARD_ATTRIBUTE_DEFINITION>
<GROUP_NUMBER>0008</GROUP_NUMBER>
<ELEMENT_NUMBER>0115</ELEMENT_NUMBER>
<NAME>Coding Scheme Name</NAME>
<VR>ST</VR>
<VM>1</VM>
</STANDARD_ATTRIBUTE_DEFINITION>
<STANDARD_ATTRIBUTE_DEFINITION>
```

-continued

```
        <GROUP_NUMBER>0008</GROUP_NUMBER>
        <ELEMENT_NUMBER>1000</ELEMENT_NUMBER>
        <NAME>Network ID</NAME>
        <RETIRED>RET</RETIRED>
    </STANDARD_ATTRIBUTE_DEFINITION>
```

At runtime, the repository 48 of FIG. 4 maintains an in-memory copy of the data dictionary documents 45. When the parser 42 encounters a new attribute, the parser 42 queries the repository 48, using, for example, the 4 byte hex tag for the definition of this attribute. Since the parser 42 can natively understand the data types, the parser can interpret the attribute and build an in-memory array of DICOM attributes. This array of DICOM attributes is encoded into a metadata document 49 according to the specification by the XML mapping document 46.

XML Mapping Document

A mapping document defines how a DICOM attribute should be encoded into an XML element of the metadata document. A default XML metadata schema and the associated mapping document 46 is provided. When an application designer overwrites the default XML metadata schema with his own, the new XML metadata schema is parsed to build a new mapping document corresponding to the new XML metadata schema. The XML mapping document contains a flat list of attribute tags and their corresponding XPath, which points out the destination of a DICOM attribute in a metadata document, as illustrated below:

```
<XML_MAPPING_DOCUMENT>
    <XPATH_MAPPING>
<ATTRIBUTE_TAG>00080020</ATTRIBUTE_TAG>
        <PATH>/DICOM_METADATA/NAMED/STUDY/GENERAL_STUDY/STU
        DY_DATE</PATH>
</XPATH_MAPPING>
    <XPATH_MAPPING>
<ATTRIBUTE_TAG>00080030</ATTRIBUTE_TAG>
        <PATH>/DICOM_METADATA/NAMED/STUDY/GENERAL_STUDY/STU
        DY_TIME</PATH>
</XPATH_MAPPING>
...
<XML_MAPPING_DOCUMENT>
```

In this example, the DICOM standard attribute study date that has the tag (0008,0020) maps into an XML metadata element "STUDY_DATE" at the XML tree location "/DICOM_METADATA/NAMED/STUDY/GENERAL_STUDY/". Similarly, the DICOM attribute study time maps to an XML metadata element "STUDY_TIME". Suppose the DICOM standard attribute STUDY DESCRIPTION (0008, 1030) has not been listed by the XML mapping document, but exists in a DICOM object therefore appears in a DICOM metadata document, the resulting metadata document will look like the following:

```
<DICOM_METADATA>
    <NAMED>
        ...
        <STUDY>
            ...
            <GENERAL_STUDY>
            ...
```

-continued

```
                <STUDY_DATE>a_date_value</STUDY_DATE>
                <STUDY_TIME>a_time_value</STUDY_TIME>
                ...
            </GENERAL_STUDY>
            ...
        </STUDY>
        ...
    </NAMED>
    <UNNAMED>
        ...
        <LONG_STRING definerRef="DICOM" tag="00081030"
        definition="Study
    description">value</LONG_STRING>
        ...
    </UNNAMED>
<DICOM_METADATA>
```

As shown, if an attribute is not defined individually in the XML mapping document, then it is mapped to the unnamed part of the DICOM metadata document.

XML Metadata Schema Definition

The XML metadata schema and the XML mapping document must be consistent. For example, the XML metadata schema that matches the XML mapping document example in paragraph [00093] is the following:

```
<xs:element name="DICOM_METADATA">
    <xs:complexType>
    <xs:sequence>
    <xs:element name="NAMED">
        <xs:complexType>
        <xs:sequence>
        <xs:element name="STUDY">
            <xs:complexType>
            <xs:sequence>
                <xs:element name="GENERAL_STUDY">
                <xs:complexType>
                <xs:sequence>
                    <xsd:element name="STUDY_DATE"
                    type="DA" minOccurs="0"
nillable="true">
    <xsd:attribute name="definerRef" fixed="DICOM"/>
    <xsd:attribute name="tag" fixed="00080020"/>
    <xsd:attribute name="definition" fixed="patient name"/>
                    </xsd:element>
                    <xsd:element name="STUDY_TIME"
                    type="TM" minOccurs="0"
```

-continued

```
                nillable="true">
         <xsd:attribute name="definerRef" fixed="DICOM"/>
         <xsd:attribute name="tag" fixed="00080030"/>
         <xsd:attribute name="definition" fixed="study time"/>
                  </xsd:element>
               </xs:sequence>
             </xs:complexType>
          </xs:element> <!-- GENERAL STUDY -->
        </xs:sequence>
      </xs:complexType>
    </xs:element> <!-- STUDY -->
   </xs:sequence>
  </xs:complexType>
 </xs:element> <!--NAMED SECTION-->
 <xs:element name="UNNAMED" type=DATASET">
 </xs:element> <!--UNNAMED SECTION-->
 </xs:sequence>
 </xs:complexType>
</xs:element> <!-- DICOM_METADATA-->
```

In the above, the unqualified data types such as "DA", "TM" and "DATASET" are all defined in the DICOM data type definition schema. The XML metadata schema can be customized by an administrator at installation time. A default metadata schema is defined that includes the attributes from the following information entity in the named section: patient, specimen, clinical trials, study, series, equipment, image, waveform, and SOP common. The rest of the DICOM standard attributes and all private attributes are encoded in the unnamed section by default. The only restriction on the schema is that it must use data types that are consistent (can be cast into) to what have been defined in the DICOM data type schema.

In general, named attributes have a structure that is semantically important. For example, the "GENERAL_STUDY" element contains a sub-element "STUDY_DATE", and the latter is an attribute qualifies the former. Having such a structure can improve the readability and usability of an XML document. One may optionally model DICOM macros and information entity definition in his own schema. The advantages of modeling them according to the DICOM standard definition is that one may enforce some level of standard conformance with XML schema alone. The disadvantage is that such schema definition is likely to be affected by the frequent changes of the DICOM standard.

EXAMPLES

Customizing the XML Metadata Schema

An administrator may easily customize the XML metadata schema. If a database application frequently queries the DICOM attribute STUDY DESCRIPTION (0008,1030), the administrator may customize the XML metadata schema to include this attribute as a named attribute. This can be easily achieved by adding an additional entry to the XML mapping document:

```
<xsd:element name="STUDY_DESCRIPTION" type="LO"
       minOccurs="0" nillable="true">
  <xsd:attribute name="definerRef" fixed="DICOM"/>
  <xsd:attribute name="tag" fixed="00081030"/>
      <xsd:attribute name="definition" fixed="study description"/>
</xsd:element>
```

Note that sometimes, it is possible to automatically generate the metadata schema from a mapping document and a DICOM data dictionary.

One may annotate the XML schema to specify the mapping from XML data types to SQL types and to specify additional storage directives. The benefit of such customization is better data organization and higher performance.

Transforming an XML Document

A document may be easily transformed from one XML metadata schema into another. The transformation can be illustrated using the previous example of STUDY_DESCRIPTION. A table is created using the first schema where STUDY_DESCRIPTION is an unnamed element. If at a later time, it is determined that STUDY_DESCRIPTION is used frequently in the application and the STUDY_DESCRIPTION into the NAMED attribute section can be moved to improve code readability and the performance of retrieval. The XML mapping document and XML metadata schema is customized. A column is created and added to the original database table, and the column is bound to the new schema. The metadata documents can be transformed in the original column into the new column. Because both schemas conforms to the same data type definition, the following line can be removed from the unnamed section of the original document:

<LONG_STRING definerRef="DICOM" tag="00081030" definition="Study description">value</LONG_STRING> and a new line inserted in the named section of the new document:

<STUDY_DESCRIPTION>value</STUDY_DESCRIPTION>

Figure 5:
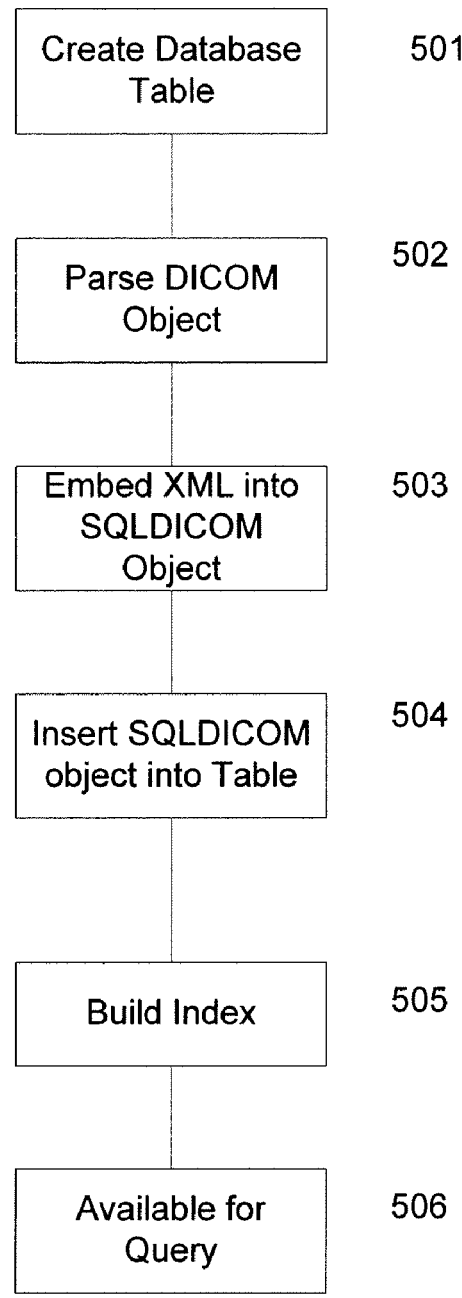
FIG. 5 is a flowchart of one embodiment of a method incorporating features of the present invention.

Referring to Fig. 5, one embodiment of a process is illustrated. A database table is created 501. A DICOM object is parsed 502. An XML representation is embedded 503 in to a SQLDICOM object. The SQLDICOM object is inserted 504 into the table. An index is built 505, and the object is available 506 for query.

The value of the new element is exactly the same as the original value because both elements have the same data type. The tag in the named element has its specific name. It is not necessary to include the element attributes such as definerRef and tag, since they are specified as fixed attributes in element definitions of the XML metadata schema.

Figure 6:
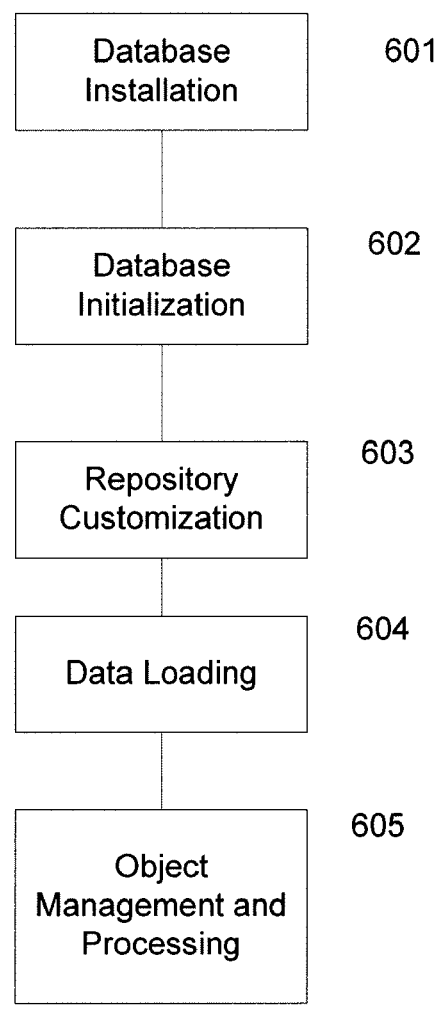
FIG. 6 is a flowchart of one embodiment of a method incorporating features of the present invention.

Referring to FIG. 6, one embodiment of a Sample Process Flow incorporating features of the present invention is illus-

```
<XPATH_MAPPING>
<ATTRIBUTE_TAG>00081030</ATTRIBUTE_TAG>
    <PATH>/DICOM_METADATA/NAMED/STUDY/GENERAL_STUDY/STU
    DY_DESCRITION</PATH>
</XPATH_MAPPING>
``` and an additional entry to the named section of the XML metadata schema:

trated. Initially, a database application is installed 601. This can include, for example the installation of a relational database, such as for example an ORACLE™ database, is installed. In one embodiment, along with an ORACLE™ database application, a database server DICOM package, such as for example ORACLE interMEDIA™, is installed, Java and PL/SQL stored procedures for DICOM are loaded into the database. Configuration documents are loaded into the repository and the DICOM feature is ready for use.

Database initialization 602 can include loading configuration documents, including DICOM standard data dictionary, DICOM private data dictionary, XML mapping document, constraint definition documents, and preference documents, for example. The completeness and correctness of all configuration documents is validated. If the constraint document is not precompiled, the constraint module can be invoked to pre-compile the constraint definition document and the result is saved for example in the repository 48 of FIG. 4.

An optional step can include repository customization 603. Although shown as occurring only once after Database Initialization 602, this step can occur more than once. The administrator submits one or more configuration documents to customize the repository. The repository verifies the correctness and completeness of the new configuration document. If the configuration document is invalid, the repository 48 rejects the change and returns one or more error messages. If the configuration document is valid, the new configuration document will be stored in the repository 48. Examples of customization of configuration documents can include for example:

i. Modifying the standard data dictionary (e.g. add new DICOM attributes or overwrite existing ones)
ii. Modify/add new private data dictionary
iii. Change preference
iv. Change conformance requirement (add/delete/modify constraint documents)
v. Change XML metadata schema and load new XML mapping document Depending on the design, the changes can be effective at the next user connection or immediately after the configuration document is validated and accepted by the repository.

After the repository customization is complete, data loading 604 (runtime) takes place. In one embodiment, data loading 604 can comprise using SQL*Loader or other suitable methods to load DICOM images into a user defined schema and tables (BLOB column). Data loading can also include creating a database object to manage DICOM objects when uploading DICOM images into a database table.

DICOM object management and processing 605 (runtime) can include the user connecting to the database schema storing DICOM objects. The DICOM package (runtime) is initialized by initializing the repository, and creating an in-memory copy of the configuration document. The DICOM package stored procedure static initialization can optionally include creating in-memory data structures. DICOM management and processing functions can be invoked on one or more DICOM objects stored in the database. Completion of the DICOM processing session can include for example, reclaiming system resources allocated during the initialization of the DICOM package and the user ending the database connection.

DICOM object management and processing functions (runtime) can include parsing the DICOM attributes, encoding the DICOM attributes into XML and returning the XML encoding of the DICOM attribute. The DICOM object can be stored in a database column of type BLOB, BFILE, or a predefined SQL object type. Optionally, the DICOM object may also be stored at an external location pointed to by, for example a URL, in which case the content will first be imported into a temporary LOB before reading.

Figure 7A:
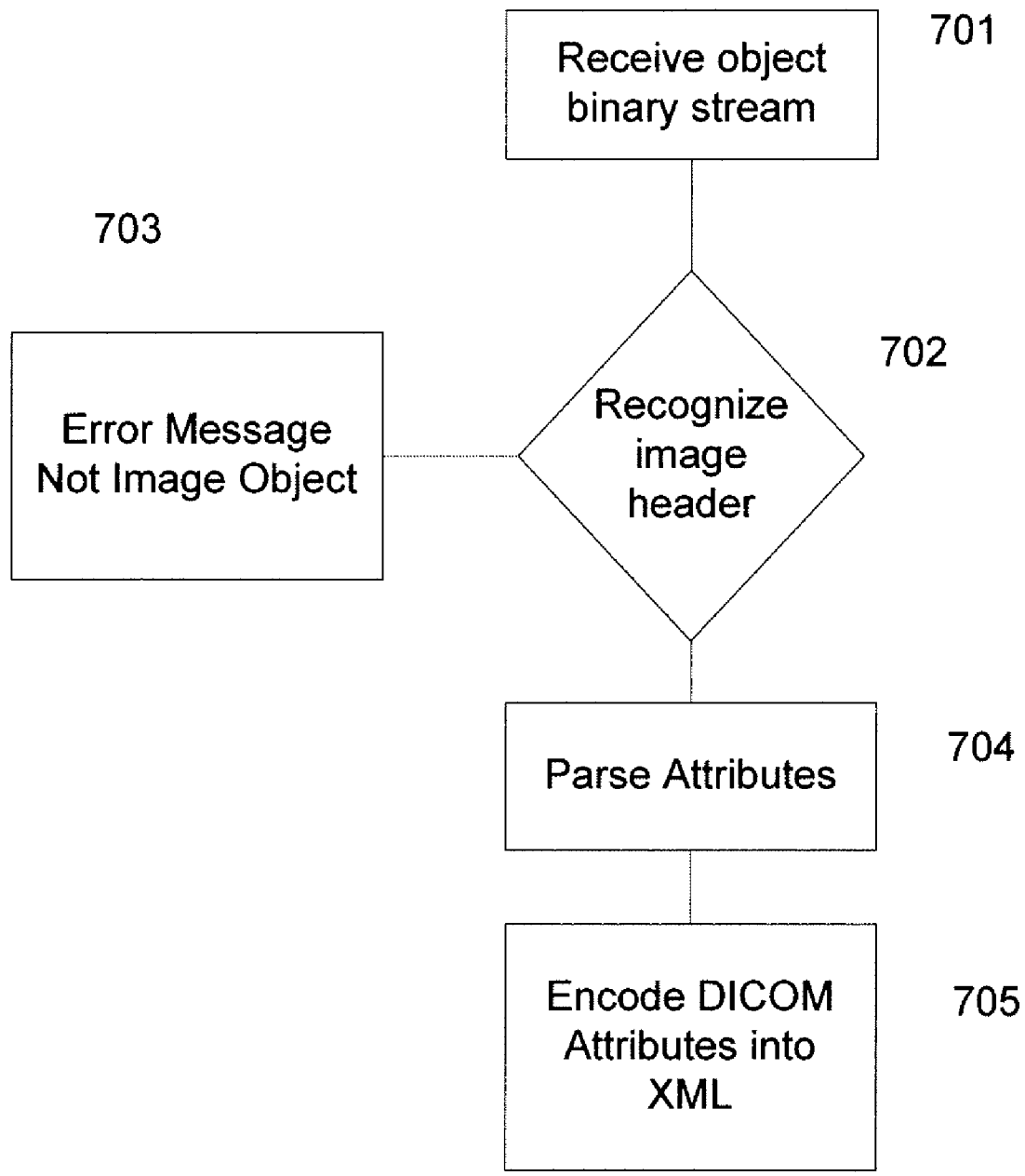
FIG. 7A is a flowchart of one embodiment of a method for metadata extraction incorporating features of the present invention.
Figure 7B:
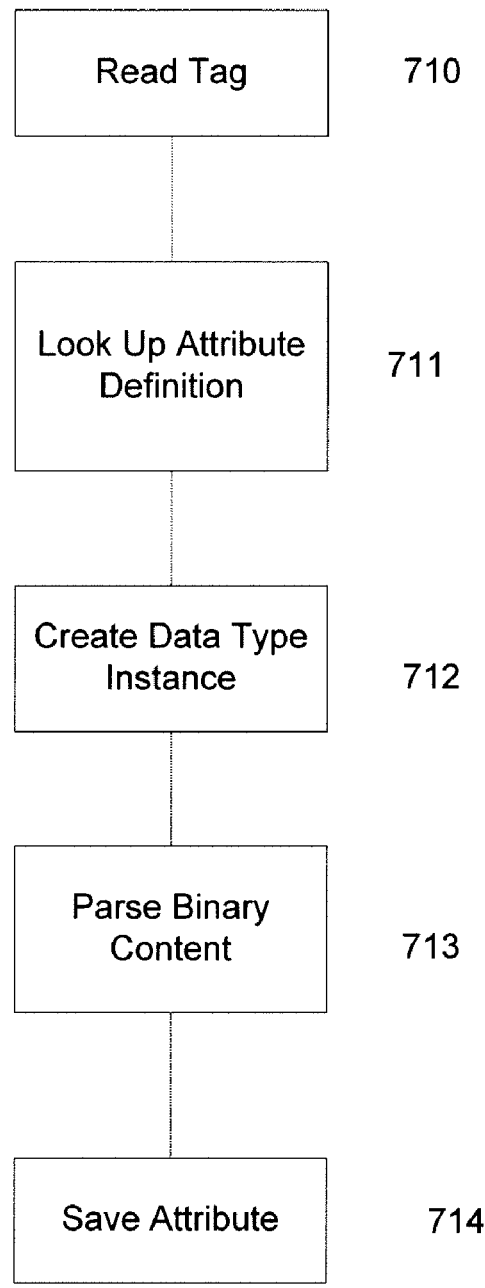
FIG. 7B is a flowchart of one embodiment of a method for parsing attributes of a DICOM object incorporating features of the present invention.
Figure 7C:
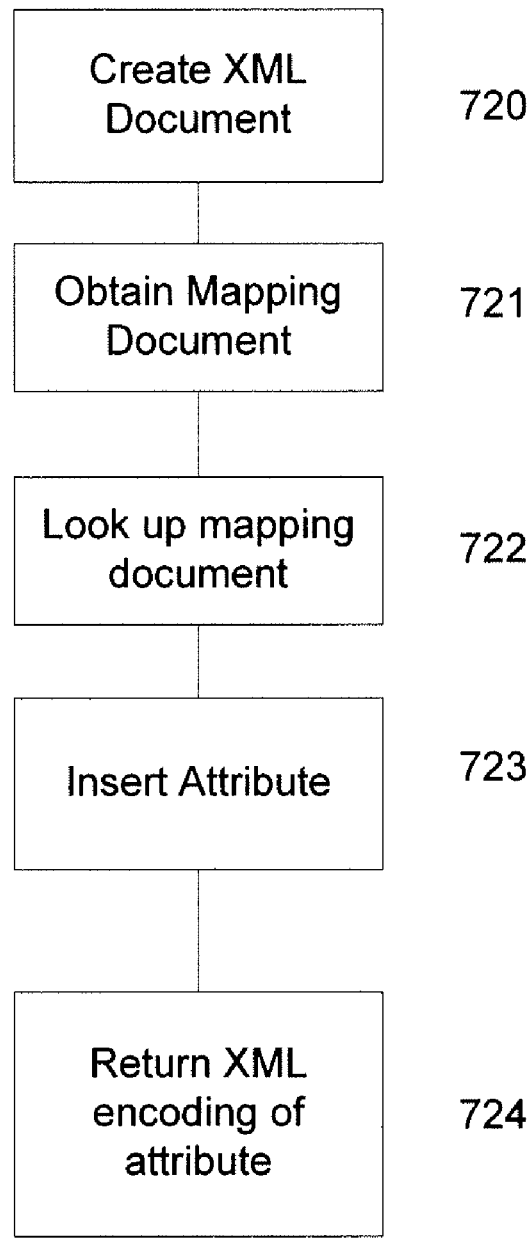
FIG. 7C is a flowchart of one embodiment of a method for encoding DICOM attributes into XML incorporating features of the present invention.

Referring to FIG. 7A, one embodiment of a metadata extraction process flow is illustrated.
i. The stored procedure gets the DICOM object handle (binary stream) 701.
ii. The stored procedure recognizes 702 the DICOM header. If the object is not a DICOM object, an error message 703 can be returned.
iii. The attributes of the DICOM object are parsed 704. Referring to FIG. 7B, in one embodiment, parsing the attributes of the DICOM object can include:
   a) For each attribute, its tag is read 710. The tag, as defined by the DICOM standard, is a 4 byte hexadecimal number.
   b) The attribute definition is looked up 711 through the data repository.
   c) A data type instance is created 712 and the binary content of the instance is parsed 713.
   d) The attribute is saved 714, which, in one embodiment can comprise a hash table.
iv. The DICOM attributes are encoded 705 into XML. Referring to FIG. 7C, one embodiment of encoding the DICOM attributes into XML is illustrated.
   a) An empty XML document is created 720.
   b) The mapping document is obtained 721, such as for example getting the XMLMapping document.
   c) For each attribute, its target XPath from XMLMapping document is looked up 722 by its tag.
   d) The attribute is inserted 723 into the XML document, at a location designated by the XPath.
v. The XML encoding of the DICOM attribute is returned 724.

Because our XSD does not strictly enforce standard conformance, a non-conformant DICOM object may be transformed into a non-conformant XML document and vice versa. If one would like to enforce standard conformance, one shall use a constraint document to specify and enforce conformance rules.

Figure 8:
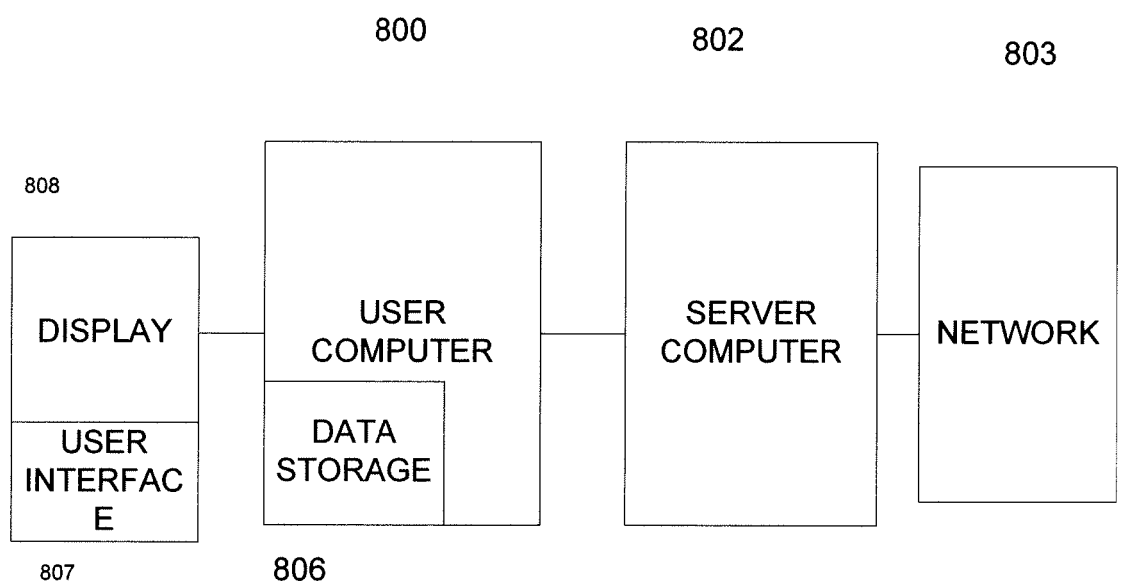
FIG. 8 is a block diagram of one embodiment of a typical architecture that can be used to practice the disclosed embodiments.

The present invention may also include software and computer programs incorporating the process steps and instructions described above that are executed in different computers. FIG. 8 is a block diagram of one embodiment of a typical apparatus incorporating features of the present invention that may be used to practice the present invention. As shown, a computer system 800 may be linked to another computer system 802, such that the computers 801 and 802 are capable of sending information to each other and receiving information from each other. In one embodiment, computer system 802 could include a server computer adapted to communicate with a network 803, such as for example, the Internet. Computer systems 800 and 802 can be linked together in any conventional manner including a modem, hard wire connection, or fiber optic link. Generally, information can be made available to both computer systems 800 and 802 using a communication protocol typically sent over a communication channel or through a dial-up connection on ISDN line. Computers 800 and 802 are generally adapted to utilize program storage devices embodying machine readable program source code which is adapted to cause the computers 800 and 802 to perform the method steps of the present invention. The program storage devices incorporating features of the present invention may be devised, made and used as a component of a machine utilizing optics, magnetic properties and/or electronics to perform the procedures and methods of the present invention. In alternate embodiments, the program storage devices may include magnetic media such as a diskette or computer hard drive, which is readable and executable by a computer. In other alternate embodiments, the program storage devices could include optical disks, read-only-memory ("ROM") floppy disks and semiconductor materials and chips. In one embodiment a computer program product comprises a computer useable medium having computer readable code means embodied therein for causing a computer to integrate medical data and images in a database system. the computer readable code means in the computer program product comprising: computer readable program code means for causing a computer to read a contents of a medical image data object, the contents including image data and metadata; computer readable program code means for causing a computer to convert the medical image data object into an array of attributes from a set of attribute definitions stored in a data dictionary; computer readable program code means for causing a computer to map the array of attributes into a metadata document that corresponds to rules in an XML mapping document; and computer readable program code means for causing a computer to store the metadata document as a structured query language medical image data object in the database system.

Computer systems 800 and 802 may also include a microprocessor for executing stored programs. Computer 800 may include a data storage device 806 on its program storage device for the storage of information and data. The computer program or software incorporating the processes and method steps incorporating features of the present invention may be stored in one or more computers 800 and 802 on an otherwise conventional program storage device. In one embodiment, computers 800 and 802 may include a user interface 807, and a display interface 808 from which features of the present invention can be accessed. In one embodiment, the user interface 807 and the display interface 808 comprise a single device or graphical user interface. The user interface 807 and the display interface 808 can be adapted to allow the input of queries and commands to the system, as well as present the results of the commands and queries.

The disclosed embodiments define an XML schema definitions of the metadata for managing DICOM objects in a database. The advanced schema satisfies the requirements of compactness, extensibility for accommodating standard updates and customization, and atomicity. One schema is used to represent all DICOM objects and ensures correct data movement between XML and DICOM. Attributes of a DICOM object are managed by introducing a new classification of DICOM attributes that include shared attributes and application specific attributes. The disclosed embodiments provide precise one to one lossless mapping, ensure standard conformance and a fully constrained XML schema definition for application specific attributes.

What is claimed is:

1. A method of integrating Digital Imaging and Communication in Medicine (DICOM) images into a database management system comprising:

creating, in a memory, a database table with at least one table column of a database object type for at least one DICOM image object encapsulated with the database object type including at least one shared attribute and at least one application specific attribute that comprises a schema-bound XML representation of metadata associated with a corresponding DICOM image object;

parsing, using at least a processor, the corresponding DICOM image object using a database stored procedure and generating the schema-bound XML representation of metadata associated with the corresponding DICOM image object where the schema-bound XML representation of metadata includes shared attribute elements organized hierarchically and allows the shared attribute elements to be addressed by a fixed path, and application specific attribute elements organized in a list according to a value representative of the application specific attribute elements and allows the application specific attribute elements to be addressed by an element tag;

enabling bi-directional mapping of the schema-bound XML representation of metadata and the corresponding DICOM image object, where the schema-bound XML representation is convertible back into a syntactically valid DICOM image object using the bi-directional mapping;

saving the metadata in the schema-bound XML representation of metadata associated with the corresponding DICOM image object; and inserting the database object in the at least one table column, of the database object type, of the table.

2. The method of claim 1 where parsing the DICOM image object further comprises:

looking up an attribute definition for each attribute;

creating a data type instance for each attribute and parsing the binary content of the data type instance; and saving each attribute together with the data type instance in a data structure.

3. The method of claim 1 where creating the schema-bound XML representation of metadata associated with the DICOM image object comprises:

creating an empty XML document;

obtaining a mapping document;

looking up, in the mapping document, a target for each attribute by the tag; and inserting each attribute in a data structure.

4. The method of claim 3 wherein a unique identifier comprises an SOP instance UID.

5. The method of claim 1 further comprising building an index on an image column in the database.

6. The method of claim 1 further comprising mapping a single DICOM object into multiple XML formats to serve different application needs.

7. The method of claim 1 further comprising that the XML schema definition of metadata associated with the DICOM image object includes a fixed core segment and an extensible segment, the fixed core segment composed of DICOM object attributes and the extensible segment composed of specific DICOM implementations to define a one to one bi-directional mapping between a DICOM datatype and the XML schema definition.

8. A method of using a database management system to manage Digital Imaging and Communication in Medicine (DICOM) images comprising:

creating a database table with at least one column for a database object of a database object type that includes a schema-bound XML representation of a DICOM image object;

designing a metadata schema for the XML representation of the DICOM image object and associating the schema with an XML namespace designated to a default XML metadata schema where the default XML metadata schema includes shared attribute elements organized hierarchically and allows the shared attribute elements to be addressed by a fixed path, and application specific attribute elements organized in a list according to a value representative of the application specific attribute elements and allows the application specific attribute elements to be addressed by an element tag;

loading the database object with the default XML metadata schema into the database;

inserting the database object into the table with a unique identifier; and enabling bi-directional mapping of the XML representation to-and-from the DICOM image object, where a resultant DICOM image object that is generated from transforming the schema-bound XML representation is bitwise identical to the DICOM image object.

9. The method of claim 8 where designing the metadata schema further comprises:

parsing attributes of the DICOM image object;
encoding the attributes into XML; and
returning the XML encoding of the DICOM image object to be associated with the database object.

10. The method of claim 9 where parsing attributes of the DICOM image object further comprises:

reading a tag associated with each attribute;
associating an attribute definition with each attribute;
creating a data type instance and parsing a binary content of the data type instance; and
saving each attribute in a data structure.

11. A method of creating an XML schema definition for a Digital Imaging and Communication in Medicine (DICOM) image comprising:

defining shared attributes;
defining application specific attributes;
mapping the shared attributes and the application specific attributes; and
defining the XML metadata schema representing the DICOM image, the XML metadata schema having a fixed core segment that organizes shared attribute elements hierarchically and allows the shared attribute elements to be addressed by a fixed XPath and an extensible segment that organizes application specific attribute elements in a list according to a value representative of the application specific attribute elements and allows the application specific attribute elements to be addressed by an element tag;
enabling bi-directional mapping of the DICOM image with an XML metadata schema representation by utilizing the XML metadata schema.

12. The method of claim 11 wherein the shared attributes are patient, specimen, clinical trials, general study, patient study, general series, clinical trial series, general equipment, image pixel, waveform identification, waveform and SOP common attributes.

13. The method of claim 11 wherein the XSD conforms to a VR definition and explicitly lists all subfields, defining a complex type comprising three subcomponents, a unibyte, a ideographic and a phonetic subcomponent.

14. The method of claim 11 where any valid XML document can be encoded into a syntactically valid DICOM standalone file and a syntactically valid DICOM standalone file can be mapped into a valid XML document.

15. The method of claim 11, where providing the bi-directional mapping of the XML metadata schema and the corresponding DICOM image object includes:

generating a bi-directional mapping where the XML metadata schema representing the DICOM image object is convertible with lossless transformation back into the DICOM image object based at least in part on the bi-directional mapping; and
storing the bi-directional mapping in a memory.

16. A method for managing digital images and communication in Digital Imaging and Communication in Medicine (DICOM) objects in a database comprising:

defining a XML schema comprising a fixed core segment that organizes shared attribute elements hierarchically and allows the shared attribute elements to be addressed by a fixed XPath and an extensible segment that organizes application specific attribute elements in a list according to a value representative of the application specific attribute elements and allows the application specific attribute elements to be addressed by an element tag;
including only attributes common to all DICOM objects in the fixed core segment;
including a sequence of data element descriptors in the extensible segment;
extracting metadata from the corresponding DICOM image object;
encoding the extracted metadata into an XML representation of the metadata and associate the XML representation with the XML schema; and
enabling bi-directional mapping of the DICOM image object with the XML representation.

17. The method of claim 16 wherein attributes in the fixed core segment are patient, series or study.

18. A system for managing Digital Imaging and Communication in Medicine (DICOM) image data comprising:

a relational database stored in a memory including tables that store DICOM images and data; and
at least one DICOM image object stored in a memory that is mapped to an XML metadata document by defining a XML schema comprising a fixed core segment that organizes shared attribute elements hierarchically and allows the shared attribute elements to be addressed by a fixed XPath and an extensible segment that organizes application specific attribute elements in a list according to a value representative of the application specific attribute elements and allows the application specific attribute elements to be addressed by an element tag;
including only attributes common to all DICOM objects in the fixed core segment;
including a sequence of data element descriptors in the extensible segment;
extracting metadata from the corresponding DICOM image object;
encoding the extracted metadata into an XML representation of the metadata and associate the XML representation with the XML schema; and
enabling bi-directional mapping of the DICOM image object with the XML representation by utilizing the XML metadata schema.

19. The system of claim 18 further comprising an XML mapping document for converting the DICOM image object into an XML element.

20. The system of claim 18 further comprising:

a data dictionary including a set of DICOM image attribute definitions;
a mapping document defining mapping rules for mapping the DICOM image attributes into a metadata document; and
a constraint document for validating a standard conformance of the metadata document with DICOM imaging standards.

21. A computer-readable medium that stores executable instructions that are non-transitory and that when executed by an apparatus cause the apparatus to perform a method, the method comprising:

creating, in a memory, a database table with at least one table column of a database object type for at least one DICOM image object encapsulated with a database object type including at least shared one attribute and at least one application specific attribute that comprises a schema-bound XML representation of metadata associated with the corresponding DICOM image object;

parsing, using at least a processor, the corresponding DICOM image object using a database stored procedure and generating the schema-bound XML representation of metadata associated with the corresponding DICOM image object where the schema-bound XML representation of metadata includes shared attribute elements organized hierarchically and allows the shared attribute elements to be addressed by a fixed path and application specific attribute elements organized in a list according to a value representative of the application specific attribute elements and allows the application specific attribute elements to be addressed by an element tag;

enabling bi-directional mapping of the schema-bound XML representation of metadata and the corresponding DICOM image object, where the schema-bound XML representation is convertible back into a syntactically valid DICOM image object using the bi-directional mapping;

saving the metadata in the schema-bound representation of metadata associated with the corresponding DICOM image object; and inserting the database object in the at least one table column, of the database object type, of the table.

* * * * *

UNITED STATES PATENT AND TRADEMARK OFFICE
CERTIFICATE OF CORRECTION

Page 1 of 1

PATENT NO. : 7,853,621 B2
APPLICATION NO. : 11/285977
DATED : December 14, 2010
INVENTOR(S) : Dongbai Guo It is certified that error appears in the above-identified patent and that said Letters Patent is hereby corrected as shown below:

In column 1, line 30, delete "extensible" and insert -- eXtensible --, therefor.

In column 5, line 41, before "of" insert -- method --.

In column 6, line 32, delete "in" and insert -- In --, therefor.

In column 9, line 17, delete "identical" and insert -- identical. --, therefor.

In column 15, line 15, delete ""=DATASET">" and insert -- ="DATASET"> --, therefor.

In column 15, line 62, delete "DY_DESCRITION" and insert -- DY_DESCRIPTION --, therefor.

In column 16, line 42-47, delete "Referring to Fig. 5, one embodiment of a process is illustrated. A database table is created 501. A DICOM object is parsed 502. An XML representation is embedded 503 in to a SQLDICOM object. The SQLDICOM object is inserted 504 into the table. An index is built 505, and the object is available 506 for query." and insert the same below "schema." on Col. 16, Line 54 as a next paragraph.

In column 19, line 8, delete "system." and insert -- system, --, therefor.

Signed and Sealed this
Ninth Day of August, 2011

David J. Kappos
*Director of the United States Patent and Trademark Office*